United States Patent [19]

Nakamura et al.

[11] 3,962,436

[45] June 8, 1976

[54] PHARMACEUTICAL COMPOSITIONS HAVING CONTROLLED RATE OF GASTRO-INTESTINAL ABSORPTION

[75] Inventors: Toshio Nakamura, Ibaraki; Tadao Maeda, Ibaraki; Hiroshi Takenaka, Ibaraki; Yoshiya Yamahira, Takatsuki, all of Japan

[73] Assignee: Sumitomo Chemical Company, Limited, Japan

[22] Filed: Aug. 22, 1974

[21] Appl. No.: 499,572

Related U.S. Application Data

[62] Division of Ser. No. 40,358, May 25, 1970, Pat. No. 3,849,558.

[30] Foreign Application Priority Data

June 3, 1969 Japan.............................. 44-43895
Jan. 30, 1970 Japan.............................. 45-8619

[52] U.S. Cl................................ 424/233; 424/229; 424/252; 424/274; 424/312; 424/320; 424/324; 424/358
[51] Int. Cl.² .............. A61K 31/615; A61K 31/635; A61K 31/525; A61K 47/00
[58] Field of Search ........... 424/320, 324, 312, 252, 424/229, 233, 274, 358

[56] References Cited

UNITED STATES PATENTS

| 3,472,931 | 10/1969 | Stoughton | 424/320 |
|---|---|---|---|
| 3,784,577 | 1/1974 | Fukumaru | 424/320 |

OTHER PUBLICATIONS

Sumitomo – Chem. Abst. vol. 71 (1969), p. 79708j.

*Primary Examiner*—Sam Rosen
*Attorney, Agent, or Firm*—Wenderoth, Lind & Ponack

[57] ABSTRACT

Pharmaceutical compositions with controlled rates of gastro-intestinal absorption are prepared by dissolution or suspension of the therapeutically active agent in an absorption depressive agent selected from the group consisting of unsaturated aliphatic alcohols or their esters, unsaturated aliphatic ethers, unsaturated aliphatic acids or their salts, their esters or their amides and natural occurring oils containing more than 35% by weight of any of the above-mentioned substances, said absorption depressive materials having 12 – 22 carbon atoms in their unsaturated aliphatic hydrocarbon chains and being liquid at the normal temperature.

8 Claims, No Drawings

PHARMACEUTICAL COMPOSITIONS HAVING CONTROLLED RATE OF GASTRO-INTESTINAL ABSORPTION

This is a division of application Ser. No. 40,358, filed May 25, 1970, now U.S. Pat. No. 3,849,558.

This invention relates to a pharmaceutical composition with a long-lasting effect by controlling gastro-intestinal absorption of an active therapeutic agent, and to a method of producing the same.

It is important to mollify or prolong the effect of a therapeutically active agent. In fact, there have been made various proposals to maintain the therapeutic effect for a prolonged period of time. Thus, there is known a process for producing a pharmaceutical composition with a long-lasting effect by melting or mixing a therapeutically active agent with a release-delaying material such as a natural or synthetic water-insoluble compound, resin or wax and forming the mixture into granules, tablets or the like (for example, refer to U.S. Pat. Nos. 3065143, 3074852, 3279998, 3330729, 3332633, 3336200, 3362881, 3388041, etc.). There is also known a method wherein granules or tablets containing an active therapeutic agent are coated with such release-delaying material (for example, refer to U.S. Pat. Nos. 2738303, 2963402, 3383283, etc.). However, in any event, such known processes are to obtain a composition which is solid at the normal temperature and therefore have various disadvantages. For instance, the operation is complicated and requires special instruments so that the cost of the production is expensive. In addition to the above, not only a well trained technique is required to get a satisfactory drug-release rate but also due to such phenomena as the strain relaxation or the polymorphism of the solid release-delaying material, the drug-release rate at the time of the production of the composition is likely to change with the lapse of time. Further, the obtained solid composition is so large that it is difficult or improper to administer the same to small animals in order to test the absorption of the active medicament.

We have found that when a certain compound having unsaturated hydrocarbon chain in the molecule is administered together with a therapeutically active agent, the gastro-intestinal absorption of the therapeutically active agent is controlled or delayed. Thus, when a therapeutically active agent is dissolved or suspended in such absorption depressive material, there is obtained a medicinal composition which, even if a liquid form, has a controlled rate of gastro-intestinal absorption and therefore a controlled duration of the therapeutic effect.

Thus the present invention provides a pharmaceutical composition having controlled gastro-intestinal absorption rate of a therapeutically active agent, said composition comprising a therapeutically effective amount of the therapeutically active agent and an equivalent or more amount to weight to the therapeutically active agent of absorption depressive material selected from the group consisting of unsaturated aliphatic alcohols or their esters, unsaturated aliphatic ethers, unsaturated aliphatic acids or their salts, their esters or their amides and natural occurring oils containing more than 35 % by weight of any of the above-mentioned substances, said absorption depressive materials having 12–22 carbon atoms in their unsaturated aliphatic hydrocarbon chains and being liquid at the normal temperature.

The present invention further provides a process for preparing a pharmaceutical composition having controlled gastro-intestinal absorption rate of a therapeutically active agent, which comprises dissolving or suspending the therapeutically active agent into an equivalent or more amount by weight to the therapeutically active agent of absorption depressive material selected from the group consisting of unsaturated aliphatic alcohols or their esters, unsaturated aliphatic ethers, unsaturated aliphatic acids or their salts, their esters or their amides and natural occurring oils containing 35 % or more by weight of any of the above-mentioned substances, said absorption depressive material having 12 – 22 carbon atoms in their unsaturated aliphatic hydrocarbon chains, and being liquid at the normal temperature.

In the present invention, the pharmaceutical composition is prepared by merely dissolving or suspending a therapeutically active agent together with or without its water-soluble salt into an above-mentioned amount of the absorption-depressive material.

If desired, to the above absorption-depressive material, there may be further added an absorption controlling material selected from the group consisting of surface active agent such as Tween homologues, Span homologues, sucrose fatty acid esters and cellulose fatty acid esters, and glycols such as polyethylene glycol, propylene glycole and glycerin.

In the process of the present invention, the operation conditions such as temperature, etc. are not limited specifically and the operation is simpler and takes a shorter time for completion than in a process for obtaining a conventional long-lasting pharmaceutical composition and no special mechanical apparatus and skill are required. Therefore, according to the invention, the production cost is greatly lowered. Further, the rate of absorption can be controlled easily as one wishes simply by selecting proper absorption depressive material and absorption controlling material varying the materials to be used. Thus a long-acting oral preparation or suppository can be obtained very easily. Further, there is no such instability of the drug-release rate as has been a great defect of a solid composition, and the personal difference of the amount of absorption is also little. Further, it is possible to administer the present composition to ordinaly small animals to test the efficacy so that one can develop a long-acting preparation quickly, reasonably and objectively.

The pharmaceutical composition of this invention in the form of solution or suspension may be administered as such to a living body or may be used as contained in a capsule with the addition of a suitable solubilizing agent, coloring agent, corrigent, inactive additives or stabilizer as required.

As described above, the absorption depressive material to be used in this invention for characteristic depression of the gastro-intestinal absorption of a therapeutic agent are ethylenically or acetylenically unsaturated aliphatic alcohols and their esters, ethylenically or acetylenically unsaturated aliphatic ethers, ethylenically or acetylenically unsaturated aliphatic fatty acid and their salts, esters and amides and natural oils containing more than 35 % by weight of any of those materials. These materials are liquid at the normal temperature and have 12 to 22 carbon atoms in their unsaturated hydrocarbon chain. Examples of natural substances which may be used as such absorption depressive materials are linoleic acid, linolenic acid, safflower oil, castor oil, peanut oil, etc. among which castor oil is most preferable.

Examples of acid moiety of the ester of the unsaturated aliphatic alcohol include alk($C_1$-$C_4$)ylcarboxylic acid, cyclo-alk($C_5$-$C_7$)ylcarboxylic acid, benzylcarboxylic acid, alk($C_1$-$C_4$)ylbenzylcarboxylic acid, benzoic acid and alk($C_1$-$C_4$)yl-, halogen- or amino-substituted benzoic acid.

Examples of the unsaturated aliphatic ether include di-unsaturated aliphatic ether and alkyl unsaturated aliphatic ether.

Examples of alcohol moiety of the ester of the unsaturated aliphatic acid include alk($C_1$-$C_4$)ylalcohol, cycloalk($C_5$-$C_7$)ylalcohol, phenol benzylalcohol, alk($C_1$-$C_4$)ylbenzylalcohol, and alk($C_1$-$C_4$)yl-, halogen- or amino-substituted phenol. Examples of amine moiety of the amide of the unsaturated aliphatic acid include alk($C_1$-$C_4$)ylamine, cycloalk($C_5$-$C_7$)ylamine, benzylamine, alk($C_1$-$C_4$)ylbenzylamine, aniline and alk($C_1$-$C_4$)yl-, halogen- or hydroxy-substituted aniline.

As for synthetic absorption depressive materials, there may be exemplified methyl linolate, N-cyclohexyl linoleamide and N-α-methylbenzyl linoleamide, among which N-α-methylbenzyl linoleamide is most preferable.

Generally the larger the amount of the absorption depressive material, the higher the release-delaying effect. The absorption depressive material may be used in an amount of about 1.5 to 200 or 65 to 200 times the therapeutic agent to be used.

As mentioned before, the absorption controlling materials which are used for the purpose of controlling the action of the absorption depressive material are surface active agents such as Tween homologues, Span homologues, sucrose fatty acid esters and cellulose fatty acid esters, and glycols such as polyethylene glycols, propylene glycols and glycerin.

Such absorption controlling material may be used in any desired amount depending upon the extent of control over the absorption depressive material. However, generally, it is preferable to be used in an amount of 10 to 50 % by weight on the absorption depressive material.

It is an important advantage of the present invention that, by varying the proportion of the absorption controlling material to the absorption depressive material, the rate of absorption of the therapeutic agent can be easily adjusted over a very wide range.

The present invention can be applied to any therapeutic agent such as, for example, barbiturates such as phenobalbital; salicylic acid or the like such as aspirin; sulfonamide such as sulfisoxazale; steroids such as estradiol; alkaloids such as ergotamine; indolyl aliphatic acid derivatives; vitamines such as riboflavin; antibiotics such as chlorampheniral; and their esters and amides; benzodiazepine derivatives such as Diazepam and Oxazepam.

The amount of such therapeutic agent should be, preferably, less than 50 % by weight of the absorption depressive material.

In the present invention, the more the therapeutic agent is oleophilic, the longer the gastrointestinal absorption is prolonged.

The advantage of the present invention is most effectively obtained, if the therapeutic agent is basic or acidic substance, by using a mixture of the therapeutic agent and its water-soluble salt because the action of the absorption depressive material is different between to basic or acidic substance and its water-soluble salt. Under the depressed absorption, the basic or acidic substance is absorbed gradually while the part of its water-soluble salt is absorbed quickly so that, after the administration, the therapeutic effect may be developed quickly and may be maintained for a long time. The basic or acidic substance and water-soluble salt may be used in any desirable proportion. However, it is preferable that the amount of the water-soluble salt is less than 70 % by weight based on the total therapeutic agent.

Examples of the salt include alkali metal salt, alkaline earth metal salt, salt of an organic base such as a basic amino acid, hydrochloride, sulfate or salt of a mono-, di- or tri-carboxylic acid having 2–6 carbon atoms.

The invention will be illustrated in the following examples. But the present invention is not at all limited to them.

EXAMPLE 1

150 mg. of chloramphenicol palmitate were dissolved in 3 g. of castor oil at 50° to 60°C. to obtain a release-delaying preparation of chloramphenicol palmitate. The cumulative recovery rate of the urinary excretion with the lapse of time when the composition of this example was orally administered to a human is shown in Table 1 wherein 150 mg. of a powder of chloramphenicol palmitate was used as a control.

EXAMPLE 2

150 mg. of chloramphenicol palmitate were dissolved in 300 mg. of castor oil at 50° to 60°C. and the solution was filled into a gelatin capsul to obtain a release-delaying preparation of chloramphenicol palmitate. The cumulative recovery rate of the urinary excretion with the lapse of time when the composition of this example was orally administered to a human is shown in Table 1 wherein 150 mg. of a powder of chloramphenicol palmitate was used as a control.

EXAMPLE 3

150 mg. of chloramphenicol palmitate were dissolved in 3 g. of N-α-methylbenzyl linoleamide at 50° to 60°C. to obtain a release-delaying preparation of chloramphenicol palmitate. The cumulative recovery rate of the urinary excretion with the lapse of time when the composition of this example was orally administered to a human being is shown in Table 1 wherein 150 mg. of a powder of chloramphenicol palmitate was used as a control.

EXAMPLE 4

150 mg. of chloramphenicol palmitate were dissolved in 300 mg. of N-α-methylbenzyl linoleamide at 50° to 60°C. and the solution was filled into a gelatin capsul to obtain a sustained release preparation of chloramphenicol palmitate. The cumulative recovery rate of the urinary excretion with the lapse of time when the composition of this example was orally administered to a human being is shown in Table 1 wherein 150 mg. of a powder of chloramphenicol palmitate was used as a control.

EXAMPLE 5

150 mg. of chloramphenicol palmitate were dissolved in 3 g. of a mixture of peanut oil and N-α-methylbenzyl linoleamide at a ratio of 1:2 at 50° to 60°C. to obtain a release-delaying preparation of chloramphenicol palmitate in the state of a liquid. The cumulative recovery rate of the urinary excretion with the lapse of time when the composition of this example was orally administered to a human is shown in Table 1 wherein 150 mg. of a powder of chloramphenicol palmitate was used as a control.

EXAMPLE 6

86.3 mg. of chloramphenicol were suspended in 3 g. of castor oil to obtain a release-delaying preparation of chloramphenicol plamitate in the form of a suspension. The cumulative recovery rate of the urinary excretion with the lapse of time when the composition of this example was orally administered to a human is shown in Table 1 wherein 86.3 mg. of a powder of chloramphenicol palmitate was used as a control.

EXAMPLE 7

20 mg. of riboflavin butyrate were dissolved in 3 g. of castor oil at 40° to 50°C. to obtain a release-delaying preparation of riboflavin butyrate in the form of a liquid. The cumulative recovery rate of the urinary excretion with the lapse of time when the composition of this example was orally administered to a human is shown in Table 1 wherein 20 mg. of a powder of riboflavin butyrate was used as a control.

EXAMPLE 8

20 mg. of riboflavin butyrate were dissolved in 3 g. of N-α-methylbenzyl linoleamide at 40° to 50°C. to obtain a release-delaying preparation of riboflavin butyrate in the form of liquid. The cumulative recovery rate of the urinary excretion with the lapse of time when the composition of this example was orally administered to a human is shown in Table 1 wherein 20 mg. of a powder of riboflavin butyrate was used as a control.

EXAMPLE 9

100 mg. of sulfisoxazole were suspended in 3 g. of N-α-methylbenzyl linoleamide to obtain a release-delaying preparation of sulfisoxazole in the form of a liquid. The cumulative recovery rate of the urinary excretion with the lapse of time when the composition of this example was orally administered to a human is shown in Table 1 wherein 100 mg. of a powder of sulfisozazole was used as a control.

EXAMPLE 10

100 mg. of salicylic acid were dissolved in 400 mg. of N-α-methylbenzyl linoleamide at 50° to 60°C. and the solution was filled into a gelatin capsul to obtain a release-delaying preparation of salicyclic acid. The cumulative recovery rate of the urinary excretion with the lapse of time when the composition of this example was orally administered to the human is shown in Table 1 wherein 100 mg. of a powder of salicylic acid was used as a control.

EXAMPLE 11

200 mg. of indomethacin were dissolved in 2 g. of castor oil at 40° to 50°C. to obtain a release-delaying preparation of indomethacin. The concentration in blood with the lapse of time when the composition of this example was orally administered to a human is shown in Table 2 wherein 200 mg. of a powder of indomethacin was used as a control.

EXAMPLE 12

200 mg. of indomethacin were dissolved in 2 g. of a mexture consisting of castor oil and tween at a ratio of 2:1 at 40° to 50°C. to obtain a release-delaying preparation of indomethacin in the form of a liquid. The concentration in blood with the lapse of time when the composition of this example was orally administered to a human is shown in Table 2 wherein 200 mg. of a powder of indomethacin was used as a control.

EXAMPLE 13

150 mg. of chloramphenicol palmitate were dissolved in 3 g. of peanut oil at 50° to 60°C. to obtain a release-delaying preparation of chloramphenicol palmitate in the form of a liquid. The cumulative recovery rate of the urinary excretion with the lapse of time when the composition of this example was orally administered to a human is shown in Table 1 wherein 150 mg. of a powder of chloramphenicol palmitate was used as a control.

EXAMPLE 14

150 mg. of chloramphenicol palmitate were dissolved in 3 g. of safflower oil at 50° to 60°C. to obtain a release-delaying preparation of chloramphenicol palmitate in the form of a liquid. The cumulative recovery rate of the urinary excretion with the lapse of time when the composition of this example was orally administered to a human is shown in Table 1 wherein 150 mg. of a powder of chloramphenicol palmitate was used as a control.

EXAMPLE 15

150 mg. of chloramphenicol palmitate were dissolved in 3 g. of linseed oil at 50° to 60°C. to obtain a release-delaying preparation of chloramphenicol palmitate in the form of a liquid. The cumulative recovery rate of the urinary excretion with the lapse of time when the composition of this example was orally administered to human is shown in Table 1 wherein 150 mg. of a powder of chloramphenicol palmitate was used as a control.

EXAMPLE 16

150 mg. of chloramphenicol palmitate were dissolved in 3 g. of a mixture consisting of propylene glycol and N-α-methylbenzyl linoleamide at a ratio of 1:1 at 50 to 60°C. to obtain a release-delaying preparation of chloramphenicol palmitate in the form of a liquid. The cumulative recovery rate of the urinary excretion with the lapse of time when the composition of this example was orally administered to a human is shown in Table 1 wherein 150 mg. of chloramphenicol palmitate was used as Control 1 and 3 was used as Control 2.

EXAMPLE 17

150 mg. of chloramphenicol palmitate were dissolved in 3 g. of a mixture consisting of propylene glycol and N-α-methylbenzyl linoleamide at a ratio of 1:3 at 50° to 60°C. to obtain a release-delaying preparation of chloramphenicol palmitate in the form of a liquid. The cumulative recovery rate of the urinary excretion with the lapse of time when the composition of this example was orally administered to the human is shown in Table 1 wherein 150 mg. of a powder of chloramphenicol palmitate was used in Control 1 and Example 3 was used as Control 2.

EXAMPLE 18

50 mg. of salicylic acid were dissolved in 400 mg. of N-α-methylbenzyl linoleamide at 40° to 50°C., and 58 mg. of sodium salicylate (corresponding to 50 mg. of salicylic acid) were suspended in the solution. The mixture was filled into a gelatin capsul to obtain a release-delaying preparation of salicylic acid. The cumulative recovery rate of the urinary excretion with the lapse of time when the composition of this example was orally administered to a human is shown in Table 1 wherein 100 mg. of a powder of salicylic acid was used as Control 1 and Example 10 was used as Control 2.

EXAMPLE 19

150 mg. of indomethacin were dissolved in 2 g. of castor oil at 40° to 50°C. to obtain a release-delaying preparation of indomethacin in the form of a liquid. The concentration in blood with the lapse of time when the composition of this example was orally administered to a rabbit is shown in Table 2 wherein 150 mg. of a powder of indomethacin was used as a control.

EXAMPLE 20

75 mg. of indomethacin were dissolved in 2 g. of castor oil at 40° to 50°C. and 80 mg. of sodium indomethacinate (corresponding to 75 mg. of indomethacin) were suspended in the solution to obtain a release-delaying preparation of indomethacin in the form of a liquid. The concentration in blood with the lapse of time when the composition of this example was orally administered to a rabbit is shown in Table 2 wherein 150 mg. of a powder of indomethacin was used as Control 1 and Example 19 was used as Control 2.

EXAMPLE 21

150 mg. of indomethacin were dissolved in 1.875 g. of N-α-methylbenzyl linoleamide at 40° to 50°C. and the solution was filled into a gelatin capsule suitable for the administration to the rectum to obtain a release-delaying suppository of indomethacin. The concentration in blood with the lapse of time when the above mentioned sustained release suppository was administered to the rectum of a rabbit is shown in Table 2 wherein, as a control, there was used 150 mg. of indomethacin dissolved in 1.875 g. of polyethylene glycol and contained in the same gelatin capsule.

Table 1

| Example | Therapeutic agent | Cumulative recovery rate of urimary excretion (%) | | | |
|---|---|---|---|---|---|
| | | 3 hrs. | 6 hrs. | 9 hrs. | 12 hrs. |
| (Control) | Chloramphenicol palmitate | 8 | 57 | 75 | 85 |
| 1 | " | 2 | 20 | 32 | 40 |
| 2 | " | 5 | 35 | 53 | 62 |
| 3 | " | 0 | 8 | 13 | 17 |
| 4 | " | 1 | 8 | 28 | 35 |
| 5 | " | 1 | 13 | 25 | 43 |
| 13 | " | 2 | 47 | 66 | 76 |
| 14 | " | 3 | 37 | 56 | 65 |
| 15 | " | 3 | 25 | 36 | 43 |
| 16 | " | 3 | 38 | 55 | 65 |
| 17 | " | 2 | 15 | 27 | 37 |
| (Control) | Chloramphenicol | 10 | 20 | 28 | 34 |
| 6 | " | 7 | 17 | 21 | 25 |
| (Control) | Riboflavin butyrate | 19 | 51 | 62 | 68 |
| 7 | " | 3 | 25 | 42 | 45 |
| 8 | " | 5 | 32 | 45 | 49 |
| (Control) | Sulfisoxazole | 11 | 21 | 27 | 32 |
| 9 | " | 5 | 12 | 17 | 22 |
| (Control) | Salicylic acid | 37 | 49 | 52 | 54 |
| 10 | " | 17 | 31 | 37 | 40 |
| 18 | Salicylic acid and sodium salicylate | 29 | 37 | 42 | 44 |

Table 2

| Example | Therapeutic agent | Test animal | Concentration in blood (mcg./ml.) | | | | | |
|---|---|---|---|---|---|---|---|---|
| | | | 1 hr. | 2 hrs. | 3 hrs. | 4 hrs. | 6 hrs. | 8 hrs. |
| (Control) | Indomethacin | Man | 5.1 | 7.3 | 6.0 | 3.2 | 1.2 | — |
| 11 | " | " | 0.7 | 1.0 | 0.7 | 0.7 | 0.8 | — |
| 12 | " | " | 2.7 | 3.4 | 3.0 | 2.5 | 2.3 | — |
| (Control) | Indomethacin | Rabbit | 4.7 | 45.7 | 25.3 | 20.0 | 9.1 | — |
| 19 | " | " | 2.9 | 2.1 | 5.9 | 18.8 | 14.9 | 10.5 |
| 20 | Indomethacin and sodium indomethacin | " | 1.8 | 18.8 | 14.1 | 20.3 | 8.4 | 14.5 |
| (Control) | Indomethacin | Rabbit | 34.6 | 21.4 | 15.6 | 5.6 | 4.6 | 1.8 |
| 21 | " | " | 10.5 | 9.1 | 7.3 | 11.2 | 6.9 | 8.6 |

What we claim is:

1. A pharmaceutical composition having a controlled gastro-intestinal absorption rate of a therapeutically active agent selected from the group consisting of chloramphenicol, chloramphenicol palmitate, riboflavin, riboflavin butyrate, sulfisoxazole, salicyclic acid, indomethacin and pharmaceutically acceptable water soluble salts thereof, said composition comprising a therapeutically effective amount of said therapeutically active agent and an equivalent or more by weight to said therapeutically active agent of N-α-methylbenzyl linoleamide.

2. A composition as claimed in claim 1 wherein the linoleamide is N-α-methylbenzyl linoleamide and the therapeutically active agent is indomethacin.

3. A composition as claimed in claim 1 wherein the linoleamide is N-α-methylbenzyl linoleamide and the therapeutically active agent is salicyclic acid.

4. A composition as claimed in claim 1 wherein the linoleamide is N-α-methylbenzyl linolamide and the therapeutically active agent is chloramphenicol palmitate.

5. A composition as claimed in claim 1 wherein the linoleamide is N-α-methylbenzyl linoleamide and the therapeutically active agent is riboflavin butyrate.

6. A pharmaceutical composition according to claim 1 wherein the amount of the absorption depressive material is 1.5 to 200 times by weight the therapeutically active agent.

7. A pharmaceutical composition according to claim 1 wherein the composition further contains an absorption containing material in an amount of 10 to 50% by weight, based on the weight of the linoleamide, of a surface active agent.

8. A pharmaceutical composition according to claim 1, wherein the composition is in the form of a solution, suspension, capsule or a suppository.

* * * * *